United States Patent [19]
Dimarogonas

[11] Patent Number: 5,402,781
[45] Date of Patent: Apr. 4, 1995

[54] METHOD AND APPARATUS FOR DETERMINING BONE DENSITY AND DIAGNOSING OSTEOPOROSIS

[75] Inventor: Andrew D. Dimarogonas, St. Louis, Mo.

[73] Assignee: Washington University, St. Louis, Mo.

[21] Appl. No.: 25,941

[22] Filed: Mar. 3, 1993

[51] Int. Cl.⁶ .................... A61B 5/00; A61B 8/00
[52] U.S. Cl. .................... 128/653.1; 128/660.01; 128/739; 128/740; 73/579; 73/584; 364/413.02
[58] Field of Search .................... 128/653.1, 739, 740, 128/774, 660.01, 744; 73/579, 584; 364/413.02

[56] References Cited

U.S. PATENT DOCUMENTS

| | | | |
|---|---|---|---|
| 4,754,763 | 7/1988 | Doemland | 128/739 |
| 4,799,498 | 1/1989 | Collier | 128/774 |
| 4,926,870 | 5/1990 | Brandenburger | 128/660.01 |
| 4,941,474 | 7/1990 | Pratt, Jr. | 128/660.01 |
| 4,976,267 | 12/1990 | Jeffcott et al. | 128/774 |
| 5,006,984 | 4/1991 | Steele | 128/744 |
| 5,143,069 | 9/1992 | Kwon et al. | 128/660.01 |

FOREIGN PATENT DOCUMENTS 9106245  5/1991  European Pat. Off. ............ 128/739

OTHER PUBLICATIONS

*The American Society of Mechanical Engineering* paper entitled *Structural Damping*, presented at a colloquium on structural damping held at the ASME annual meeting, pp. 1–34, Dec. 1959.

*Calcified Tissue International* article entitled *Material Damping for Monitoring of Density and Strength of Bones*, by Andrew D. Dimarogonas et al, 1993, 52:244–247.

*Primary Examiner*—K. M. Pfaffle
*Attorney, Agent, or Firm*—Rogers, Howell & Haferkamp

[57] ABSTRACT

The integrity (density) of discrete pieces of hard tissue (bones) in a patient may be determined by either one of two methods. In a first method, an impulse of energy is introduced into the hard tissue, such as by striking the patient's hard tissue, and the induced vibration is sensed and analyzed in order to compute the damping factor thereof, the damping factor being directly related to the density thereof. With this method, a transducer is coupled to the hard tissue and its output is amplified by an amplifier before input to a computer which determines the damping factor. In a second method, a continuous energy input is provided to the hard tissue, such as by utilizing a frequency generator coupled to a power amplifier whose output drives a transducer such as a speaker or the like for inducing a continuous vibration in the hard tissue. This continuous vibration is measured with a transducer, having amplified output, and a damping factor is calculated with a computer.

28 Claims, 2 Drawing Sheets

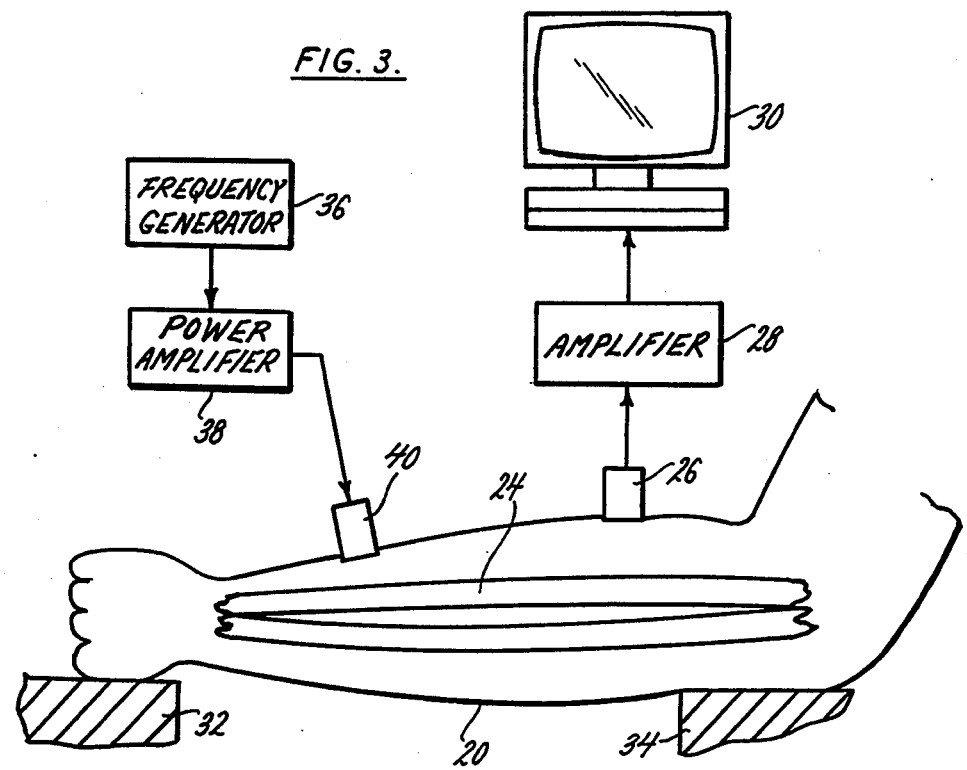
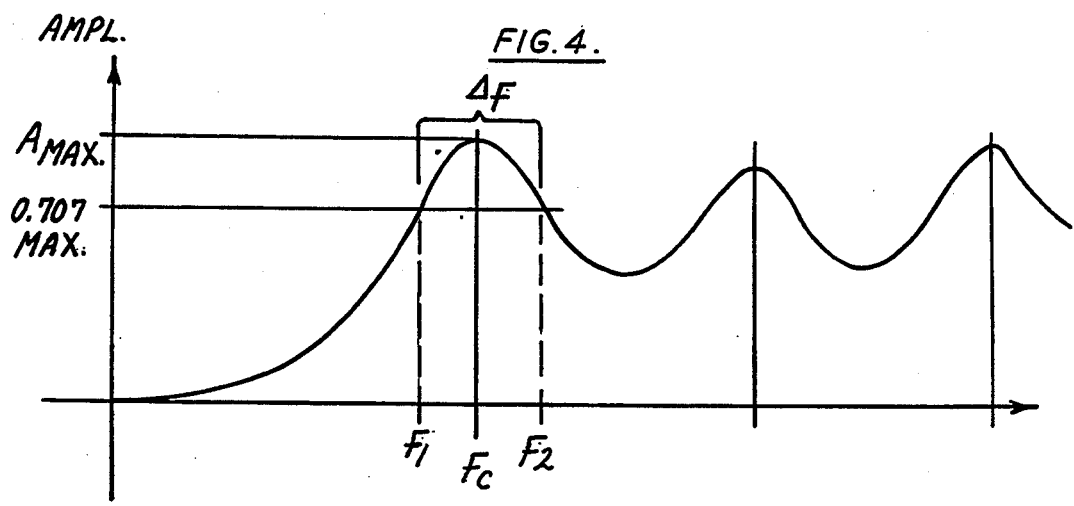

METHOD AND APPARATUS FOR DETERMINING BONE DENSITY AND DIAGNOSING OSTEOPOROSIS

BACKGROUND AND SUMMARY OF THE INVENTION

Studies of bone strength in vitro have demonstrated that the decrease in bone strength in both the spine and femur is directly proportional to the mineral content. For this reason, bone densitometry has been used extensively for the determination of bone loss in clinical diagnosis and monitoring. A variety of methods have been used, such as single and dual photon absorptiometry (SPA and DPA, respectively) and quantitative computer tomography (QCT). However, these methods are time-consuming, dependent upon the availability of sophisticated and expensive equipment, and thus expensive and ill-suited for widespread implementation. Thus, there has been a long-felt need in the prior art for a simple, efficient, and low cost methodology for measuring bone density as it is an effective diagnosis for the onset of osteoporosis, a debilitating disease commonly found in post-pregnancy and post-menopausal women. Treatment of osteoporosis is most effective if the disease is detected early whereupon hormonal treatment may be commenced. However, because of the increased risk of side effects, hormonal treatment is not desired to be begun until such time as the disease has been detected. Additionally, continuous measurement of bone density over time may readily disclose the effectiveness of treatment, leading to adjustments in the treatment protocols balanced against the attendant side effect risk.

Still another medical situation in which bone integrity is important is the healing process of bone fractures. There is a phenomenon known as non-union healing in which a bone fracture fails to knit properly to thereby return the bone to its pre-fracture integrity. Obviously, x-rays may be used to follow the healing process, but this methodology is expensive and undesirable in that it repeatedly exposes a body part to x-rays. The inventor herein has previously participated in studies which noted the relationship of the vibrational response, and specifically the determination of the natural frequency shift and phase angle shift as being related, indirectly, to the progress of fracture healing. This previous experimental work utilized cadaver bones and its application to living patients is limited for the reasons as discussed in his previously published article. See Monitoring of Fracture Healing Bilateral and Axial Vibration Analysis, *Journal of Biomechanics*, Vol. 23, No. 4, 1990.

In order to solve these and other problems in the prior art, the inventor herein has succeeded in developing a method and apparatus for determining bone integrity by measuring its vibrational response to a stimulus and determining therefrom its modal damping factor (hereinafter damping factor).

In general, the inventor has developed two techniques for measuring the damping factor of any bone or other body hard tissue. Both techniques include the basic method of coupling a transducer to the bone, the transducer having the capability of measuring the vibrational response and producing an electrical output, and then from that electrical output determining the damping factor through a programmed electronic logic device, such as a computer. In a first implementation of this method, an impulse of energy may be applied to the bone, such as by striking it, in order to generate a vibration in the bone at its natural frequency. This vibration, and its decreasing amplitude, may then be measured and used to calculate the damping factor. In a second implementation of this same method, a continuous input of energy can be applied to the bone, such as by driving a speaker with a frequency generator and coupling the speaker to the bone, such that a continuous vibrational input may be provided at about the natural frequency of the bone. Ideally, the frequency generator is adjustable so that it may be tuned to this natural frequency. The same transducer and computer may then be used to calculate the damping factor through a different mathematical analysis which depends upon the half power bandwidth of the response and its center frequency.

In proving the efficacy of the methodology disclosed and claimed herein, the inventor has conducted several experiments on bones. In doing so, the inventor has discovered that the change in the mechanical properties, such as the damping factor, is one order of magnitude greater than the corresponding change in bone density. Thus, measurement of the damping factor is sensitive to and useful in determining bone density. Furthermore, while it is desired to locate the pick-up transducer close to the bone in order to increase the measured output and amplitude of the vibrational response to thereby minimize measurement errors, it has been found that the flesh which surrounds the bone has minimal effect in the measurement as the bone dominates the damping factor effect at the lower natural frequencies not the flesh. Furthermore, as damping is a measure of the loss of strain energy during one vibratory cycle in the stress bearing part of the bone, it is relatively insensitive to the method of support for the bone. On the other hand, other mechanical properties, such as the natural frequency utilized in the inventor's prior published article depend very much on the method of support and the surrounding flesh, and are not nearly as sensitive, which thus makes those mechanical properties impractical to use in measuring and monitoring bone density levels and changes thereto over time.

The inventor's approach of using the damping factor as an indicator of bone density is also intellectually satisfying in that there is a rationale for the experimentally measured variations in the damping factor. It is generally understood and believed that loss of mass, or decrease in density, of a bone is due to the loss of mineral and a resultant void nucleation that, in turn, results in stress concentration and premature facture. This void nucleation is detected by a change in the damping factor as the bone becomes more porous and "more able" to dampen vibrations induced therein. Thus, the measurement of the damping factor is seen to be a direct measurement of this void nucleation and, hence, a direct indication of the "integrity" of the bone.

The inventor's techniques may be readily applied to the diagnosis and treatment of osteoporosis. In the first instance, the density of a particular bone of a patient may be determined by measuring its damping factor, and this particular bone's density may be determined in the same manner over time as the patient is treated, and these bone densities compared to thereby detect any changes in bone density. Obviously, a decrease in bone density in medically significant amounts would be indicative of the onset of osteoporosis. Alternately, it would be hoped that treatment, perhaps through exercise, would be helpful in increasing or at least forestalling the decrease in bone density. Thus, these techniques may be useful in measuring the effectiveness of treatments so that treatment protocols could be altered as the patient is treated over time. This methodology and use of the damping factor depends upon a relative comparison of damping factor measurements for the same bone in the same patient over time. An alternate methodology would take advantage of standardized bone density values, yet to be determined, for patients of a particular age, sex, fitness level, particular bone, etc. against which a particular patient's bone density measurement may be compared in order to determine their potential for having osteoporosis. As the inventor has recently developed the present invention, there has not been an opportunity to determine these standardized values. However, it is believed to be a straightforward matter for one of ordinary skill in the art to utilize the present invention and measure a statistically significant group of individuals in order to determine these standardized values and the particular factors important in differentiating members of the group.

While the principal advantages and features of the present invention have been described above, a more complete and thorough understanding of the invention may be attained by referring to the drawings and description of the preferred embodiment which follow.

BRIEF DESCRIPTION OF THE DRAWINGS

FIG. 3 is a diagrammatic view of the inventor's second technique for measuring bone density through the coupling of a continuous energy source to the bone; and FIG. 4 is a graph of the vibrational response induced in the bone using the technique of FIG. 3.

DETAILED DESCRIPTION OF THE PREFERRED EMBODIMENT

Figure 1:
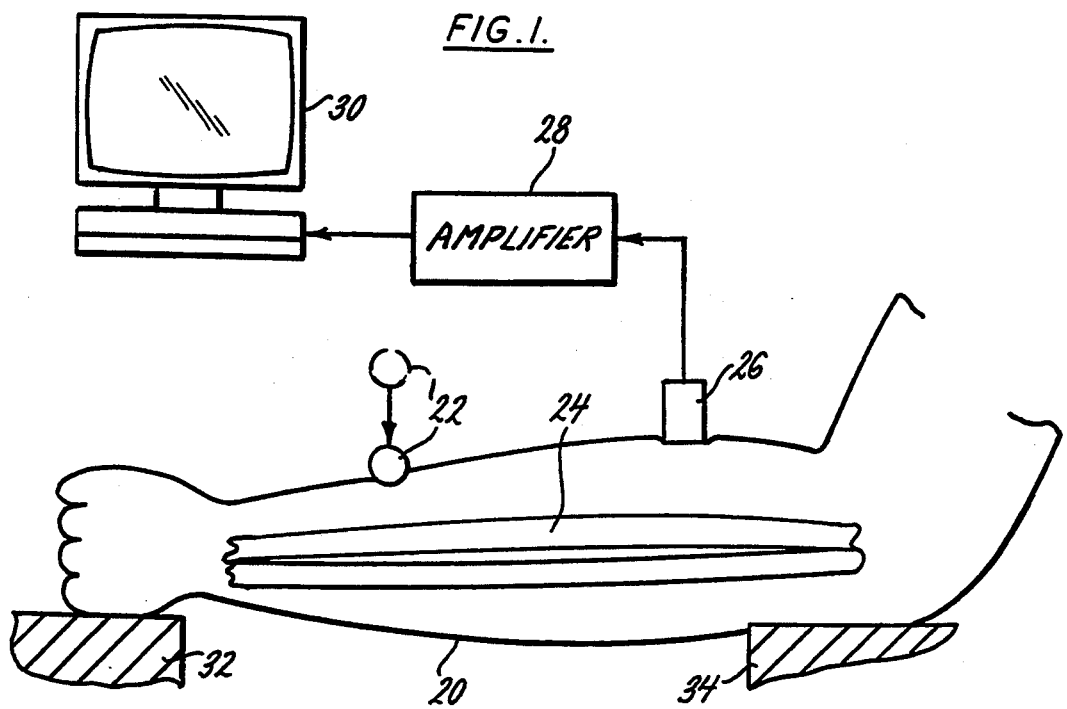
FIG. 1 is a diagrammatic view of the inventor's first technique for measuring bone density utilizing an impulse of energy input to induce a vibration into the bone.
Figure 2:
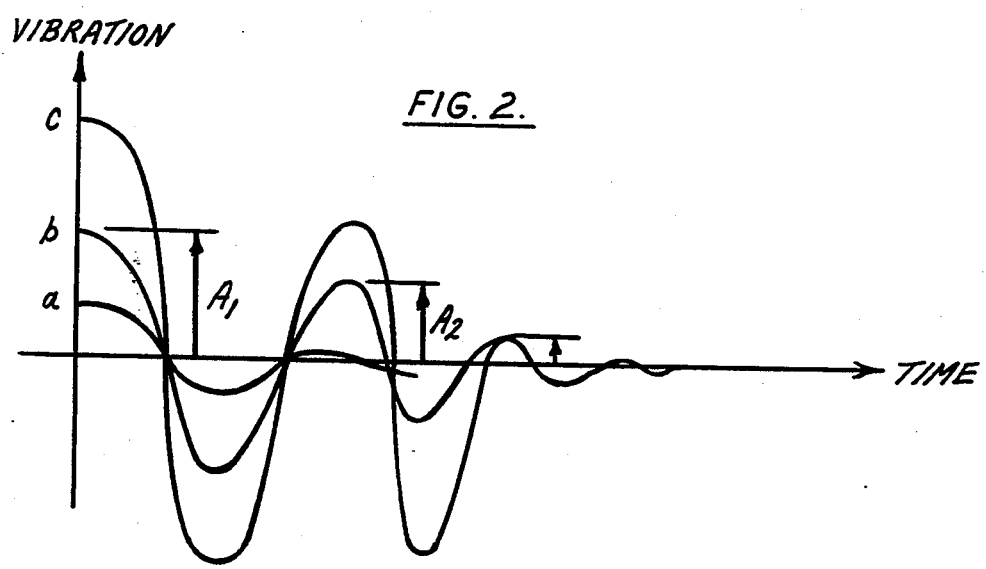
FIG. 2 is a graph of the harmonic response of vibrations induced in the bone through the technique shown in FIG. 1.

As shown in FIGS. 1 and 2, the inventor's first technique for measuring bone density includes the step of inducing a vibration in the bone desired to be measured, such as by striking a patient's arm 20 with a blunt instrument such as a rod 22 to thereby induce vibrations in a bone 24 contained within the patient's arm. For convenience, the opposite ends of the patient's arm 20 may be supported by a pair of supports 32, 34. A transducer 26 measures the induced vibration and produces an electrical output which is amplified by an amplifier 28 and then input to a computer 30 for calculation of the damping factor. As shown in FIG. 2, the vibration induced by the input of an impulse of energy into the arm 20 may have a varying amplitude corresponding to varying input force levels. The damping factor, as is well known, may be readily calculated by comparing the amplitudes of deflection successive cycles of vibration induced by any one of these initial force levels. As shown in FIG. 2, the intensity of the blow to the arm does not affect the measurement of the damping factor as the damping factor is determined by comparing two successive peak amplitudes, regardless of the size thereof. Whether the initial amplitude has an intensity of a, b, or c, there is no variation in the measured damping factor. Instead, the damping factor is determined solely by the characteristics of the bone 24 in the patient's arm 20.

As shown in FIGS. 3 and 4, an alternate technique for measuring bone damping factor may be used. As before, the patient's arm 20 has a bone 24 therein to which is mounted a transducer 26 for converting the sensed vibrational signals to an electrical signal which is then amplified by an amplifier 28 for input to computer 30. However, the initial energy input to the patient's arm 20 is achieved by way of a frequency generator 36 which produces an electrical output at a particular frequency which is then amplified by a power amplifier 38 and fed to a second transducer 40, which may be a speaker or shaker or other such device, which is coupled to the patient's arm 20. The frequency generator 36 is then tuned to frequencies sweeping through the range of the lowest natural frequencies of the patient's bone 24 to thereby produce a continuous vibrational response therein as shown in FIG. 4. A peak amplitude $F_c$ of one of the several natural harmonics induced in the patient's bone 24 is chosen for measurement of the damping factor. As is well known in the art, the damping factor is equal to the half power bandwidth $\Delta F$, or $F2-F1$, divided by the center frequency $F_c$. F1 and F2, the half power frequencies, are those frequencies at which the amplitude is 0.707 times the maximum amplitude.

The inventor has conducted two separate experiments which have proven the efficacy of utilizing the damping factor for measuring bone density. In a first experiment, chicken femoral bones were treated with hydrochloric acid for varying lengths of time, their mass was measured, and then their damping factor was determined using techniques similar to those disclosed herein. Their damping factors were then compared with the damping factors for untreated chicken femoral bones. There was found to be a direct correlation in the change of the damping factor with respect to the hours of acid treatment for the chicken femoral bones. This was to be expected as the longer the bones were immersed in the acid, the greater the reduction in their mass and hence the greater the reduction in their density. Furthermore, it was determined that the change in the damping factor was nearly one order of magnitude greater than the change in the measured density of the bone. Hence, the damping factor was considered to be highly sensitive to changes in density and a good parameter for measuring density as small changes in density could be readily detected.

In a second experiment, rat bones were utilized. More particularly, tibiae of two families of rats were compared, one family having undergone an extensive training program, it being understood that training increases bone density which should thereby show up in a reduced damping factor. Both families included members which were relatively young as well as members which were relatively old. In comparing the bones for the younger rats, it was found that training resulted in slightly lower bone density and higher damping ratio, but these changes were not considered to be statistically significant. However, in the older rats, the average change in damping factor due to training was measured at about 40% while the change in density was measured at about 23%. These experimental results prove up the beneficial results from physical exercise (training) in older individuals in maintaining the mineral content and hence density of the individual's bones. Again, the damping factor measurement was found to be significantly correlated to the density of the bones.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. A method for determining an integrity of a discrete piece of hard tissue in a subject, said method comprising the steps of:
   inducing a vibration in said discrete piece of hard tissue;
   measuring a response of the discrete piece of hard tissue to said induced vibration; and
   determining a modal damping factor of said discrete piece of hard tissue from the measured response to said vibration, said modal damping factor being representative of the integrity of said discrete piece of hard tissue.

2. The method of claim 1 further comprising the steps of repeating said steps at a spaced time interval in the same subject to thereby determine a plurality of modal damping factors and comparing said plurality of modal damping factors to thereby determine a change in the hard tissue integrity in said subject over the time interval.

3. The method of claim 2 wherein the hard tissue includes a bone, the integrity includes a density of the bone, and said method further comprises the step of diagnosing an onset of osteoporosis based upon a change in the bone density over the time interval.

4. The method of claim 2 wherein the hard tissue includes a bone, the integrity includes a continuity of the bone, and said method further comprises the step of diagnosing a non-union healing of the bone.

5. The method of claim 1 further comprising the step of comparing said modal damping factor with a standard modal damping factor to thereby determine a relative hard tissue integrity.

6. The method of claim 5 wherein the hard tissue includes a bone, the integrity includes a density of the bone, and said method further comprises the step of diagnosing an onset of osteoporosis based upon a relative bone density.

7. The method of claim 5 wherein the hard tissue includes a bone, the integrity includes a continuity of the bone, and said method further comprises the step of diagnosing a non-union healing of the bone.

8. The method of claim 1 wherein the response includes a plurality of cycles of displacement, each displacement having an amplitude and wherein the step of determining the modal damping factor includes the steps of determining the amplitudes of displacement of successive cycles of said response and comparing the amplitudes of the successive cycles to thereby determine the modal damping factor.

9. The method of claim 1 wherein the step of determining the modal damping factor includes the steps of determining a natural frequency of said discrete piece of hard tissue, determining a half power bandwidth of said response at said natural frequency, and comparing the half power bandwidth with the natural frequency to thereby determine the modal damping factor.

10. The method of claim 1 wherein the step of inducing a vibration includes the step of introducing an impulse of energy into said discrete piece of hard tissue.

11. The method of claim 10 wherein the step of introducing the impulse of energy includes the step of physically striking said discrete piece of hard tissue.

12. The method of claim 11 wherein the response includes a plurality of cycles of displacement, each displacement having an amplitude and wherein the step of determining the modal damping factor includes the steps of determining the amplitudes of displacement of successive cycles of said response and comparing the amplitudes of the successive cycles to thereby determine the modal damping factor.

13. The method of claim 12 wherein the step of measuring includes the steps of coupling a transducer to said discrete piece of hard tissue, and inputting an output of said transducer to a computer, and wherein the step of comparing the amplitudes includes the step of using the computer to calculate said comparisons.

14. The method of claim 1 wherein the step of inducing the vibration includes the step of continuously exciting said discrete piece of hard tissue with an energy source oscillating within a range substantially near a natural frequency of said discrete piece of hard tissue.

15. The method of claim 14 wherein the step of continuously exciting said discrete piece of hard tissue includes the step of varying a frequency of said energy source to thereby match said frequency to the natural frequency.

16. The method of claim 15 wherein the step of determining the modal damping factor includes the steps of determining the natural frequency of said discrete piece of hard tissue, determining a half power bandwidth of said response at said natural frequency, and comparing the half power bandwidth with the natural frequency to thereby determine the modal damping factor.

17. The method of claim 16 wherein the step of measuring includes the steps of coupling a transducer to said discrete piece of hard tissue, and inputting an output of said transducer to a computer, and wherein the step of comparing the half power bandwidth with the natural frequency includes the step of using the computer to calculate said comparisons.

18. A device for determining an integrity of a discrete piece of hard tissue in humans, said device comprising a transducer for coupling to said discrete piece of hard tissue, said transducer having means for measuring a vibrational response of said discrete piece of hard tissue, and a programmed electronic machine connected to said transducer and having means for calculating a modal damping factor of said discrete piece of hard tissue from the vibrational response of said discrete piece of hard tissue, said modal damping factor being representative of a density of said discrete piece of hard tissue.

19. The device of claim 18 further comprising an amplifier connected between said transducer and said programmed electronic machine for amplifying an output of said transducer prior to being input to said programmed electronic machine.

20. The device of claim 19 wherein said programmed electronic machine comprises a computer.

21. The device of claim 18 further comprising means for inducing a vibration in said discrete piece of hard tissue.

22. The device of claim 21 wherein said vibration inducing means comprises means for introducing an impulse of energy into said discrete piece of hard tissue.

23. The device of claim 22 wherein said vibration inducing means comprises a hard object.

24. The device of claim 21 wherein said vibration inducing means comprises means for introducing a continuous stream of energy into said discrete piece of hard tissue substantially at a natural frequency of said tissue.

25. The device of claim 24 wherein said vibration inducing means comprises a speaker and a frequency generator having an output connected to said speaker, said speaker adapted to be coupled to said discrete piece of hard tissue.

26. The device of claim 25 wherein said vibration inducing means further comprises an amplifier connected between said frequency generator and said speaker.

27. A method for diagnosing an onset of osteoporosis comprising the steps of:

determining a density of a particular bone of a subject by determining a modal damping factor of the bone;

repeating the step of determining the bone density over a period of time to thereby determine a plurality of modal damping factors; and comparing said plurality of modal damping factors to thereby detect a medically significant decrease in bone density over the period of time, said decrease being indicative of osteoporosis in the absence of other medically significant causative factors.

28. A method for diagnosing an onset of osteoporosis comprising the steps of:

determining a density of a particular bone of a subject by determining a modal damping factor of the bone;

comparing the modal damping factor with a standardized modal damping factor for a normal subject to determine any difference; and diagnosing the onset of osteoporosis based upon whether said difference represents a medically significant difference.

* * * * *